US010864178B2

(12) United States Patent
Cheong et al.

(10) Patent No.: US 10,864,178 B2
(45) Date of Patent: Dec. 15, 2020

(54) PHARMACEUTICAL COMPOSITION FOR TREATMENT OF CANCER CONTAINING POLYPHENOL COMPOUND AS ACTIVE INGREDIENT

(71) Applicants: INDUSTRY-ACADEMIC COOPERATION FOUNDATION, YONSEI UNIVERSITY, Seoul (KR); NATIONAL CANCER CENTER, Gyeonggi-do (KR)

(72) Inventors: Jae Ho Cheong, Seoul (KR); Soo Youl Kim, Gyeonggi-do (KR)

(73) Assignees: Industry-Academic Cooperation Foundation, Yonsei University; National Cancer Center

( * ) Notice: Subject to any disclaimer, the term of this patent is extended or adjusted under 35 U.S.C. 154(b) by 54 days.

(21) Appl. No.: 15/999,726

(22) PCT Filed: Feb. 17, 2017

(86) PCT No.: PCT/KR2017/001783
§ 371 (c)(1),
(2) Date: Aug. 20, 2018

(87) PCT Pub. No.: WO2017/142348
PCT Pub. Date: Aug. 24, 2017

(65) Prior Publication Data
US 2019/0388366 A1 Dec. 26, 2019

(30) Foreign Application Priority Data
Feb. 18, 2016 (KR) .................. 10-2016-0019255
Feb. 17, 2017 (KR) .................. 10-2017-0021460

(51) Int. Cl.
| A61K 31/155 | (2006.01) |
| A61K 47/59 | (2017.01) |
| A61P 35/04 | (2006.01) |
| A61K 31/4545 | (2006.01) |
| A61K 47/10 | (2017.01) |

(52) U.S. Cl.
CPC ........ *A61K 31/155* (2013.01); *A61K 31/4545* (2013.01); *A61K 47/10* (2013.01); *A61K 47/59* (2017.08); *A61P 35/04* (2018.01)

(58) Field of Classification Search
CPC .............................. A61K 31/12; A61K 31/155
See application file for complete search history.

(56) References Cited

U.S. PATENT DOCUMENTS

| 6,114,397 | A | 9/2000 | Flack et al. | |
| 8,163,805 | B2* | 4/2012 | Wang | A61K 31/11 514/682 |
| 8,574,829 | B2* | 11/2013 | Thompson | A61K 31/155 435/4 |
| 10,085,950 | B2* | 10/2018 | Kim | A61K 31/155 |

FOREIGN PATENT DOCUMENTS

| EP | 1474121 | 7/2010 |
| EP | 3111931 | 1/2017 |
| EP | 3254680 | 12/2017 |
| JP | 2010-529023 | 8/2010 |
| KR | 10-2013-0004770 | 1/2013 |
| KR | 10-2015-0102152 | 9/2015 |
| KR | 10-1904893 | 10/2018 |
| WO | WO 2005/094804 | 10/2005 |
| WO | WO 2010/056932 | 5/2010 |
| WO | WO 2010/114805 | 10/2010 |
| WO | WO 2015/130109 | 9/2015 |
| WO | WO 2016/126073 | 8/2016 |

OTHER PUBLICATIONS

Du et al., Experimental Lung Research, 2004, 30(6): 419-429(abstract).*
Saito et al., Cancer Research, 2009, 69(10): 4225-4234 (abstract).*
Xin et al. "ApoG2 as the most potent gossypol derivatives inhibits cell growth and induces apoptosis on gastric cancer cells," Biomedicine & Pharmacotherapy, 2013, vol. 67, pp. 88-95.
Del Barco et al. "Metformin: Multi-faceted protection against cancer," Oncotarget, 2011, vol. 2, No. 12, pp. 896-917.
Egan et al. "Phosphorylation of ULK1 (hATG1) by AMP-Activated Protein Kinase Connects Energy Sensing to Mitophagy," Science, Jan. 2011, vol. 331, Not. 6016, pp. 456-461.
Gunassekaran et al. "In vitro and in vivo studies on antitumor effects of gossypol on human stomach adenocarcinoma (AGS) cell line and MNNG induced experimental gastric cancer," Biochemical and Biophysical Research Communications, Jul. 2011, vol. 411, No. 4, pp. 661-666.
Han et al. AMPK/mTOR-mediated inhibition of survivin partly contributes to metformin-induced apoptosis in human gastric cancer cell, Cancer Biology & Therapy, 2015, vol. 16, No. 1, pp. 77-87.
Janzer et al. "Metformin and phenformin deplete tricarboxylic acid cycle and glycolytic intermediates during cell transformation and NTPs in cancer stem cells," PNAS, Jul. 2014, vol. 111, No. 29, pp. 10574-10579.
Kang et al. "Aldehyde dehydrogenase inhibition combined with phenformin treatment reversed NSCLC through ATP depletion," Oncotarget, Aug. 2016, vol. 7, No. 31, pp. 49397-49410.
Kato et al. "The Antidiabetic Drug Metformin Inhibits Gastric Cancer Cell Proliferation In Vitro and In Vivo," Molecular Cancer Therapeutics, Mar. 2012, vol. 11, No. 3, pp. 549-560.

(Continued)

*Primary Examiner* — Rei Tsang Shiao
(74) *Attorney, Agent, or Firm* — Sheridan Ross P.C.

(57) ABSTRACT

The present invention relates to a pharmaceutical composition for treating cancer, containing a polyphenol compound as an active ingredient. The pharmaceutical composition according to the present study is very effective for the treatment and prognosis-improvement of cancer stem cells or cancer tissues having a magnitude of cancer stem cells such as poorly differentiated cancer. Further, the polyphenol compound and a biguanide compound, and an anticancer agent were observed to remarkably increase inhibitory effects on the growth of cancerous cells when they were administered to cancerous cells in combination rather than individually, thus the composition is expected to find great applications in the cancer therapy field.

3 Claims, 12 Drawing Sheets

(56) References Cited

OTHER PUBLICATIONS

Extended Search Report for European Patent Application No. 17753509.3, dated Oct. 2, 2019, 9 pages.
Official Action for India Patent Application No. 201817033832, dated Sep. 13, 2019, 6 pages.
Official Action with English Translation for Japan Patent Application No. 2018-536492 dated Sep. 24, 2019, 12 pages.
Official Action with English Translation for Korea Patent Application No. 10-2018-0044918, dated Apr. 6, 2020, 9 pages.
International Search Report prepared by the Korean Intellectual Property Office dated Jun. 5, 2017, for International Application No. PCT/KR2017/001783.

* cited by examiner

PHARMACEUTICAL COMPOSITION FOR TREATMENT OF CANCER CONTAINING POLYPHENOL COMPOUND AS ACTIVE INGREDIENT

CROSS REFERENCE TO RELATED APPLICATIONS

This application is a national stage application under 35 U.S.C. 371 and claims the benefit of PCT Application No. PCT/KR2017/001783 having an international filing date of 17 Feb. 2017, which designated the United States, which PCT application claimed the benefit of the Republic of Korea Application No. 10-2016-0019255 filed 18 Feb. 2016 and Republic of Korea Application No 10-2017-0021460 filed 17 Feb. 2017, the disclosure of each of which are incorporated herein by reference.

TECHNICAL FIELD

The present invention relates to a pharmaceutical composition for treating cancer which contains a polyphenolic compound as an active ingredient.

BACKGROUND ART

Cancer is one of the most common causes of death worldwide. Approximately 10 million new cancer cases occur each year, and cancer accounts for approximately 12% of all death causes, which is the third leading cause of death. Accordingly, efforts have been made to develop effective anticancer drugs. However, most of the anticancer drugs developed to date, which target common cancer cells, are not effective in the death of cancer stem cells, which play an important role in the treatment resistance and recurrence of cancer. The cancer stem cells are cancer cells having the ability to renew indefinitely, like common stem cells. It is known that the cancer stem cells proliferate slowly, unlike common cancer cells, have self-renewal or differentiation ability, which is the characteristic ability of stem cells, and have a mechanism different from those of previously known cancer cells. However, until now, the development of drugs for treating cancer stem cells, which target cancer stem cells, has been very limited (Korean Patent Application No. 10-2011-0066035). When cancer stem cells remain in the body even after cancer treatment, the recurrence and/or metastasis of cancer actively occurs. For this reason, it appears that the development of drugs for treating cancer stem cells is an urgent task.

Meanwhile, gossypol as a polyphenolic compound is a phenol derivative that is contained in cotton plants in large amounts. In China, it was found that this gossypol inhibits male sperm function, and thus has been developed for use as male oral contraceptives. However, it was recently reported that gossypol has a significant effect on the inhibition of cancer cell growth (U.S. Pat. No. 6,114,397). However, it is still difficult to effectively inhibit cancer cell growth by administration of gossypol alone.

The present invention is directed to a pharmaceutical composition for treatment of cancer and cancer stem cells, which contains a polyphenolic compound as an active ingredient. The pharmaceutical composition according to the present invention is very effective for the treatment and improvement of prognosis of cancer stem cells or cancer tissues including large amounts of cancer stem cells such as poorly differentiated cancer stem cells. In addition, it was found that when the polyphenolic compound, a biguanide-based compound and an anticancer drug were administered to cancer cell in combination, the effect of inhibiting cancer cell growth was significantly increased compared to when they were administered alone, suggesting that the polyphenolic compound will be widely used in the cancer treatment field.

DISCLOSURE

Technical Problem

The present invention has been made in order to solve the above-described problems occurring in the prior art and is directed to a pharmaceutical composition for treating cancer, which contains a polyphenolic compound as an active ingredient.

However, objects which are to be achieved by the present invention are not limited to the above-mentioned objects, and other objects of the present invention will be clearly understood by those skilled in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise stated in the specification, all the scientific and technical terms used in the specification have the same meanings as commonly understood by those skilled in the technical field to which the present invention.

In one embodiment of the present invention, "cancer" is characterized by uncontrolled cell growth and refers to a state in which a cell mass called a tumor is formed by this abnormal cell growth, invades the surrounding tissue, and also metastasizes to other organs of the body in severe cases. Academically, it is also called neoplasia. Cancer is an intractable chronic disease that, even if treated with surgery, radiation, and chemotherapy, is not fundamentally cured in many cases, gives the patient pain, and ultimately leads to death. Cancer is caused by various factors which are divided into internal factors and external factors. Although a mechanism by which normal cells are transformed into cancer cells has not been clearly found, it is known that a significant number of cancers are caused by external factors such as environmental factors. The internal factors include genetic factors, immunological factors and the like, and the external factors include chemical substances, radiations, viruses and the like. Genes involved in the development of cancer include oncogenes and tumor suppressor genes, and cancer develops when a balance between these genes is lost due to the internal or external factors. Cancers can be classified according to the site of their origin into oral cancer, liver cancer, stomach cancer, colon cancer, breast cancer, lung cancer, bone cancer, pancreatic cancer, skin cancer, head cancer, neck cancer, skin cancer, cervical cancer, ovarian cancer, colorectal cancer, small bowel cancer, rectal cancer, fallopian tube carcinoma, perianal cancer, endometrial carcinoma, vaginal carcinoma, vulva carcinoma, Hodgkin's disease, esophagus cancer, lymphatic cancer, bladder cancer, gallbladder cancer, endocrine gland cancer, thyroid cancer, parathyroid cancer, adrenal gland cancer, soft tissue sarcoma, urethral cancer, penis cancer, prostate cancer, chronic leukemia, acute leukemia, lymphocytic lymphoma, renal cancer, hydroureter cancer, renal cell carcinoma, renal pelvic carcinoma, central nervous system tumor, primary central nervous system lymphoma, spinal cord tumor, brainstem glioma and pituitary adenoma, but are not limited thereto.

In one embodiment of the present invention, "poorly differentiated cancer or poorly differentiated tumor" means a state in which an indefinite arrangement of structures in cancer tissue was lost. According to the National Cancer Institute at the National Institutes of Health, the cancer classification system is based on the nature of cancer and is generally classified according to the abnormality of cancer cells into stages 1, 2, 3 and 4. Cancer in stage 1 is a cancer in which the arrangement of cancer cells is almost similar to that in normal tissue. Cancer in stage 1 has a slow rate of growth and a slow rate of invasion into the surrounding tissue. By contrast, cancer in stage 3 or 4 appears to be completely different from normal cells or normal tissue, and rapidly grows and rapidly invades the surrounding tissue compared to cancer in stage 1 or 2. This is summarized as follows Precancerous stage (GX): precancer whose stage of cancer cannot be determined;
  stage 1 (G1): well-differentiated cancer;
  stage 2 (G2): moderately differentiated cancer;
  stage 3 (G3): poorly differentiated cancer;
  stage (G4): undifferentiated cancer.

It is known that poorly differentiated cancer includes a larger amount of cancer stem cells compared to well-differentiated or moderately differentiated cancer, shows an unclear tumor boundary, metastasizes rapidly, is not effectively treated, and shows poor prognosis even after treatment.

In one embodiment of the present invention, "cancer stem cells" generally refers to cancer cells having self-renewal or differentiation ability which is the characteristic ability of stem cells. For example, cancer stem cells may include a spherical cancer cell population or a cancer tissue having an unclear shape and poor prognosis, like poorly differentiated cancer. In the normal tumor growth conditions of cancer stem cells (the "normal tumor growth conditions" refers to a state in which a nutrient (glucose) required for cell growth is sufficient and conditions for tumor microenvironment growth are abundant, and thus there is no cell stress), the cancer stem cells may proliferate at a slow rate, unlike common cancer cells, or may be maintained in a dormant state, and thus may have resistance to anticancer agents. For example, expression of transcription regulators such as PGC-1a may be controlled, unlike that in normal tumor cells, and thus the function of major metabolism regulatory substances therein may differ from that in common cancer cells. Thus, "cancer stem cells" generally refers to cells that acquire resistance to apoptosis in a nutrient-deficient state through this different metabolism regulatory ability and the regulation of cell signaling systems mechanistically linked thereto, and have invasive and/or metastatic potential. However, the cancer stem cells are not limited thereto and may include any cells that may differentiate into common cancer cells.

In one embodiment of the present invention, "inhibiting the growth of cancer stem cells" is meant to include inhibition of cancer stem cell maintenance, inhibition of cancer stem cell malignancy, and inhibition of cancer stem cell invasion.

In one embodiment of the present invention, "polyphenol" is a kind of chemical substance found in plants and is characterized in that one or more phenol groups are present in one molecule. Polyphenols are generally classified into tannins and phenylpropanoids (flavonoids, lignin, etc.). Phenols are compounds in which one hydrogen atom of benzene is substituted with a hydroxyl group, and polyphenols are compounds in which benzene is substituted with at least two hydroxyl groups. There are thousands of polyphenols, including catechins in green tea, resveratrol in wine, quercetin in apples or onions, etc. Flavonoids abundant in fruits and isoflavones abundant in beans are also examples of polyphenols.

Polyphenols prevent aging by their antioxidant effect of converting reactive oxygen species (toxic oxygen species) into nontoxic substances in the human body. It addition, it was reported that polyphenols protect DNA from damage caused by exposure to reactive oxygen species and have an excellent function of protecting cell constituent proteins and enzymes, thus reducing the risk for various diseases. However, particular polyphenols can exhibit cytotoxicity due to the action of phenol substituents. Representative examples of polyphenolic toxins include, but are not limited to, safrole, gossypol and coumarins.

In one embodiment of the present invention, "gossypol" is a kind of polyphenolic compound contained in the separable pigmented lines of the seeds, leaves, stems and roots of some of plants belonging to the genus *Gossypium* of the family Malvaceae, and is also called polyphenolic gossypol or cottonseed pigment. It renders plants resistant to pests. It was reported that gossypol was added to poultry feed, the feed utilization and the egg productivity were reduced and the yolk decolorization of stored eggs occurred. On the other hand, ruminant livestock inactivates gossypol by fermentation. Free gossypol is physiologically toxic, whereas bound gossypol is inactive. The non-protein components of cottonseeds also bind to gossypol, thereby forming non-soluble and/or non-digestible complexes. This binding detoxifies gossypol in cottonseed meal, but reduces protein and biological values. When iron is added to free gossypol at a ratio of 2:1 or 3:1, it can effectively reduce the toxicity of gossypol in the liver. In China, it was found that this gossypol inhibits male sperm function. Thus, the gossypol has been studied for use as male oral contraceptives. The gossypol in the present invention is preferably a compound represented by the following Formula 1 or a derivative thereof, but is not limited thereto:

[Formula 1]

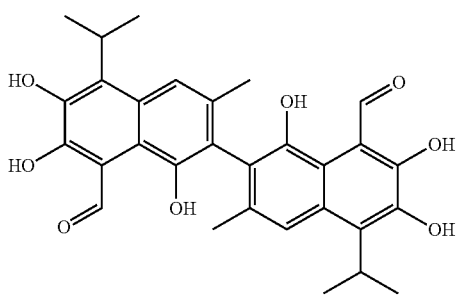

In one embodiment of the present invention, "biguanide-based compound" may preferably be a biguanide-based anti-diabetic agent, more preferably metformin, phenformin, buformine or the like. However, it is not limited thereto and may be any biguanide-based compound that induces a nutrient deficiency-like state by inhibiting intracellular energy production.

In one embodiment of the present invention, "anticancer agent" refers to a collection of chemotherapeutic agents that are used for treatment of malignant tumors. Most anticancer agents are agents that are involved in various metabolic pathways of cancer cells, thereby inhibiting the synthesis of mainly nucleic acids or exhibiting anticancer activity. Anticancer agents that are currently used for cancer treatment are classified into 6 categories based on their biochemical mechanisms of action.

(I) Alkylating agents: When very highly reactive substances having the ability to introduce an alkyl group (R—CH2) into any compound act on cells, they mostly react with N7 of guanine of DNA, deform the DNA structure, and cause chain cleavage, thereby exhibiting anticancer effects and cytotoxic effects. These drugs include ① nitrogen mustard-based drugs, including nitrogen mustard, chlorambucil, Melphalan, cyclophosphamide and the like; ② ethyleneimine-based drugs, including Thiotepa; ③ alkylsulfonate-based drugs, including busulfan; ④ triazine-based and hydrazine-based drugs, including DTIC (dacarbazine) and procarbazine; ⑤ nitrosourea-based drugs, including BCNU, CCNU, methyl-CCNU, etc.

(2) Metabolic antagonists (antimetabolites): Drugs belonging to this group act to inhibit metabolic processes required for cancer cell growth, and include ① folic acid derivatives, including methotrexate (MTX); ② purine derivatives, including 6-mercaptopurine (6-MP) and 6-thioguinine; ③ pyrimidine derivatives, including 5-fluorouracil, cytarabine, etc.

(3) Antibiotics: Among antibiotics produced from bacteria, those exhibiting anticancer activity include adriamycin, daunorubicin, bleomycin, mitomycin-C, actinomycin-D and the like.

(4) Mitotic inhibitors (vinca alkaloids): These drugs are division stage-specific drugs and stop cell division in the metaphase of mitosis. They include vincristine, vinblastine, VP-16-213 and VM-26.

(5) Hormonal agents: Any kind of cancer can be treated by administration of hormones. The use of male hormones is effective against breast cancer, and female hormones are effective against prostate cancer. Furthermore, progesterone is effective against endometrial cancer, and adrenal cortex hormones are used for treatment of acute lymphocytic leukemia or lymphoma. For breast cancer, tamoxifen, an anti-female hormonal agent, is used.

(6) Others include cisplatin, L-asparaginase, o,p-DDD and the like. As described above, about 40 anticancer drugs are currently used for the treatment of cancer, and there a great difference in anticancer spectrum between the anticancer drugs.

In one embodiment of the present invention, "irinotecan" is a kind of anticancer agent which is used against recurrent and metastatic stomach cancer, rectal cancer, colon cancer or the like. It is preferably irinotecan hydrochloride, but is not limited thereto.

In one embodiment of the present invention, "diagnosis" means confirming the presence or characteristics of a pathological condition. For the purpose of the present invention, "diagnosis" means confirming whether cancer would develop, proliferate and metastasize, and "cancer" is meant to include "cancer stem cells". Cancer can be diagnosed by visual or cytological examination of a tissue from a patient suspected of having cancer that developed or metastasized. Specifically, cancer can be diagnosed by either a method that uses a cancer-specific antibody contained in a tissue sample (clinically, cells, blood, fluid, pleural fluid, ascites, joint fluid, pus, secreted fluid, sputum, pharyngeal mucus, urine, bile juice, feces or the like) suspected of having cancer that developed or metastasized, or a method of directly detecting a cancer-related protein in the sample, or a method of directly detecting a nucleic acid encoding the cancer-related protein. Diagnostic means that use antigen-antibody binding or a method of directly detecting the cancer-related protein include, but are not limited to, Western blotting, ELISA (enzyme linked immunosorbent assay), RIA (radioimmunoassay), radioimmunodiffusion, Ouchterlony immunodiffusion, rocket immunoelectrophoresis, immunohistological staining, immunoprecipitation assay, complement fixation assay, fluorescence activated cell sorter (FACS), protein chip assay, and the like. Methods of directly detecting the nucleic acid encoding the cancer-related protein include, but are not limited to, reverse transcription-polymerase chain reaction (RT-PCR), competitive RT-PCR, real-time RT-PCR, RNase protection assay (RPA), Northern blotting, DNA chip assay or the like.

In one embodiment of the present invention, "treatment" refers to a series of actions that are performed to alleviate and/or ameliorate the disease of interest. For the purpose of the present invention, "treatment" includes actions that inhibit an increase in the number or amount of cancer cells including cancer stem cells, or kill cancer cells, or inhibit the growth of cancer tissue, or reduce the size of cancer tissue, or inhibit the development of new blood vessels in cancer tissue.

In one embodiment of the present invention, "metastasis" means that cancer cells spread from their primary organ to other organs, and "cancer", as used herein, is meant to include "cancer stem cells". The spread of cancer to other parts of the body is largely divided into one in which cancer tissue in primary cancer grows and directly invades the surrounding organs, and one in which cancer tissue metastasizes to other distant organs along blood vessels or lymphatic ducts. Metastasis can be controlled by inhibiting expression of cancer development-related genes or inhibiting the activity of the proteins encoded by the genes.

In one embodiment of the present invention, "pharmaceutical composition" refers to a composition which is to be administered for particular purposes. For the purpose of the present invention, the pharmaceutical composition according to the present invention contains a polyphenolic compound, serves to treat cancer including cancer stem cells or to inhibit the metastasis of cancer, and may contain not only a compound which is involved therein, but also a pharmaceutically acceptable carrier, excipient or diluent. Furthermore, the pharmaceutical composition according to the present invention may further contain, in addition to the polyphenolic compound, a biguanide-based compound and an anticancer agent. The biguanide-based compound is preferably phenformin, and the anticancer agent is irinotecan, but the scope of the present invention is not limited thereto. In addition, the pharmaceutical composition according to the present invention contains the active ingredient of the present invention in an amount of 0.1 to 50 wt % based on the total weight of the composition. Carriers, excipients and diluents, which may be contained in the composition of the present invention, include, but are not limited to, lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, and mineral oil.

In one embodiment of the present invention, "administering" means introducing the composition of the present invention into a patient by any suitable method. The composition of the present invention may be administered by any general route, as long as it can reach a target tissue. Specifically, the composition of the present invention may be administered orally, intraperitoneally, intravenously, intramuscularly, subcutaneously, intradermally, intranasally, intrapulmonarily, intrarectally, intrathecally, intraperitoneally or intradurally, but is not limited thereto. In the present invention, the effective amount may be controlled according to various factors, including the kind of disease, the severity of the disease, the kinds and contents of active ingredient and other ingredients contained in the composition, the type of formulation, the patient's age, weight, general health condition, sex and diet, the time of administration, the route of administration, the secretion rate of the composition, the treatment period, and drugs that are concurrently used. For adults, the pharmaceutical composition for treatment may be administered into the body in an amount of 50 ml to 500 ml for each time, the compound may be administered at a dose of 0.1 ng/kg to 10 mg/kg, and the monoclonal antibody may be administered at a dose of 0.1 ng/kg to 10 mg/kg. Regarding administration intervals, the composition may be administered 1 to 12 times a day. When the composition is administered 12 times a day, it may be administered at 2-hour intervals. In addition, the pharmaceutical composition of the present invention may be administered alone or together with other therapies known in the art, for example, chemotherapeutic agents, radiation and surgery, for treatment of the cancer stem cells of interest. Furthermore, the pharmaceutical composition of the present invention can be administered alone or in combination with other treatments designed to enhance immune responses, e.g., by co-administration with adjuvants or cytokines (or nucleic acids encoding cytokines) as known in the art. Other standard delivery methods, e.g., biolistic transfer or ex vivo treatment, can also be used. In ex vivo treatment, antigen presenting cells (APCs) such as dendritic cells, peripheral blood mononuclear cells, or bone marrow cells can be obtained from a patient or an appropriate donor and activated ex vivo with the pharmaceutical composition of the present invention, and then administered to the patient.

In one embodiment of the present invention, there is provided a pharmaceutical composition for preventing or treating cancer, which contains a polyphenolic compound as an active ingredient. The polyphenolic compound may be any one or more selected from the group consisting of safrole, gossypol and coumarins. The polyphenolic compound may be contained in an amount of 0.5 to 500 mM. The pharmaceutical composition may further contain a biguanide-based compound. The biguanide-based compound may be any one or more selected from the group consisting of metformin, buformin, and phenformin. The pharmaceutical composition may further contain an anticancer agent. The anticancer agent may be irinotecan. The cancer may include cancer stem cells. The cancer may be stomach cancer. The treating includes inhibiting an increase in the number of cancer cells including cancer stem cells, or inhibiting an increase in the amount of the cancer cells, or killing cells, or reducing or maintaining the size of a cancer tissue including cancer stem cells, or inhibiting the development of new blood vessels in a cancer tissue including cancer stem cells.

In another embodiment of the present invention, there is provided a pharmaceutical composition for inhibiting cancer metastasis, which contains a polyphenolic compound as an active ingredient. The polyphenolic compound may be any one or more selected from the group consisting of safrole, gossypol and coumarins. The polyphenolic compound may be contained in an amount of 0.5 to 500 mM. The pharmaceutical composition may further contain a biguanide-based compound. The biguanide-based compound may be any one or more selected from the group consisting of metformin, buformin, and phenformin. The pharmaceutical composition may further contain an anticancer agent. The anticancer agent may be irinotecan. The cancer may include cancer stem cells. The cancer may be stomach cancer.

Hereinafter, each step of the present invention will be described in detail.

Advantageous Effects

Cancer stem cells are cancer cells having the ability to renew indefinitely, like common stem cells. It is known that the cancer stem cells proliferate slowly, unlike common cancer cells, have self-renewal or differentiation ability, which is the characteristic ability of stem cells, and have a mechanism different from those of previously known cancer cells. When cancer stem cells remain in the body even after cancer treatment, the recurrence and/or metastasis of cancer actively occurs. For this reason, it appears that the development of drugs for treating cancer stem cells is an urgent task.

The present invention is directed to a pharmaceutical composition for treating cancer, which contains a polyphenolic compound as an active ingredient. The pharmaceutical composition according to the present invention is very effective for the treatment and improvement of prognosis of cancer stem cells or cancer tissues containing large amounts of cancer stem cells such as poorly differentiated cancer stem cells. In addition, it was found that when the polyphenolic compound, a biguanide-based compound and an anticancer drug were administered to cancer cell in combination, the effect of inhibiting cancer cell growth was significantly increased compared to when they were administered alone, suggesting that the polyphenolic compound will be widely used in the cancer treatment field.

BEST MODE

On AGS cells (hereinafter referred to as SAGS (selected AGS), Cell Death Dis. 2015 Jul. 2; 6:e1805) selected from the common stomach cancer cell line AGS (hereinafter referred to as PAGS (parental AGS)) by analyzing phenotypes, including the cancer stem cell marker expression, tumor spheroid formation and standard anticancer agent resistance of cancer cells that survived under 4 weeks of continuous metabolic stress, and tumor formation in immunosuppressed mice, the growth inhibitory effects of gossypol were examined. Cell culture and survival rate measurement methods were performed in the same manner as Example 2-1. Experimental results indicated that the $IC_{50}$ concentration of gossypol for PAGS was 4.2 mM, whereas the $IC_{50}$ concentration of gossypol for SAGS having the nature of cancer stem cells was 2.8 mM, suggesting that the sensitivity of drugs to gossypol significantly differs depending on whether the cells have the characteristics of stem cells, even though the cells are cells of the same origin.

MODE FOR INVENTION

Hereinafter, the present invention will be described in further detail. It will be obvious to those skilled in the art that these examples are for illustrative purposes only and are not intended to limit the scope of the present invention as defined in the claims.

Example 1: Examination of the Effects of Gossypol Against Stomach Cancer Cells

Example 1-1: Examination of the Proliferation Inhibitory Effects of Gossypol Against Stomach Cancer Cells In order to examine the proliferation inhibitory effects of gossypol against stomach cancer cell lines, 6 different stomach cancer cell lines (MKN28, MKN45, AGS, SNU668, Kato3 and HS746T) were prepared. The definition of cell lines known in the Korean Cell Line Bank or the American Type Culture Collection (ATCC) is described in Table 1 below.

TABLE 1

| Cell line name | Definition | Degree of differentiation |
|---|---|---|
| MKN28 | Human stomach adenocarcinoma, tubular | Moderately differentiated |
| MKN45 | Human stomach adenocarcinoma | Poorly differentiated |
| AGS | Human stomach adenocarcinoma | Poorly differentiated |
| SNU668 | Human stomach carcinoma, signet ring cell | Poorly differentiated |
| Kato3 | Human stomach carcinoma | Poorly differentiated |
| HS746T | Human stomach carcinoma | Poorly differentiated |

Figure 1:
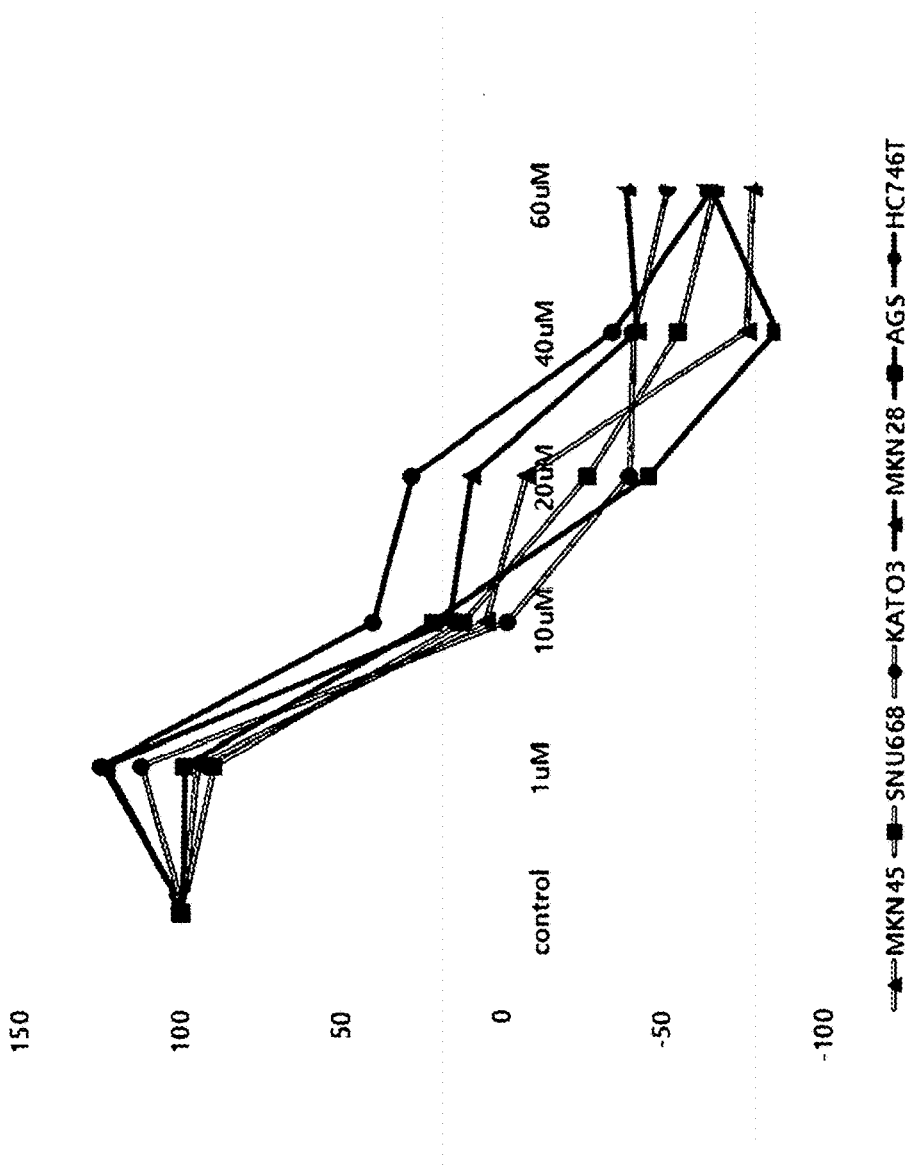
FIG. 1 shows the results of examining the proliferation inhibitory effects of gossypol against stomach cancer cell lines in an example of the present invention.

Each of the 6 different cell lines ($1 \times 10^3$ to $1 \times 10^4$ cells/well) was cultured in a 96-well plate for 24 hours, and treated with 0, 10, 20, 40 or 60 µM of gossypol, and then further cultured for 48 hours. Next, the cells were fixed with 50 vol % TCA (trichloroacetic acid) at 4° C. for 1 hour, washed with distilled water, and then dried at room temperature for a few minutes. Each well containing the fixed cells was stained with 100 µl of 0.4 wt % sulforhodamine B in 1 vol % acetic acid solution for 10 minutes, and washed four times with 1 vol % acetic acid solution. The stained plate was dried at room temperature, and then 100 µl of 10 mM Tris buffer (pH 7.5) was added to each well, and the eluted pigment was measured for its absorbance at a wavelength of 515 nm. FIG. 1 shows the growth inhibitory effects of gossypol at various concentrations against the cancer cell lines, measured as described above.

The experimental results indicated that the growth of most of the poorly differentiated cancer cells (MKN45, AGS, SNU668 and Kato3) was inhibited compared to that of the moderately differentiated cancer cells (HS746T) at all the concentrations. In addition, when the cells were treated with 60 µM of gossypol, the growth of all the poorly differentiated cancer cells (MKN45, AGS, SNU668, Kato3 and HS746T) used in the experiment was inhibited compared to that the moderately differentiated cancer cells (HS746T). The $GI_{50}$ values of gossypol for the cell lines, obtained from the above experimental results, are shown in Table 2 below.

TABLE 2

| Cell line name | $GI_{50}$ (µM) |
|---|---|
| MKN28 | 5.32 |
| MKN45 | 4.65 |
| AGS | 6.43 |
| SNU668 | 4.11 |

TABLE 2-continued

| Cell line name | GI$_{50}$ (μM) |
|---|---|
| Kato3 | 3.15 |
| HS746T | 9.89 |

Example 1-2: Examination of the ATP Synthesis Inhibitory Effects of Gossypol Against Stomach Cancer Cells ATP (adenosine triphosphate) is an energy source for organisms, and inhibition of intracellular ATP synthesis leads to a decrease in energy metabolism activity. The ATP synthesis inhibitory effects of gossypol on the stomach cancer cell lines (MKN28, MKN45 and SNU668) described in Example 1-1 were examined.

Figure 2:
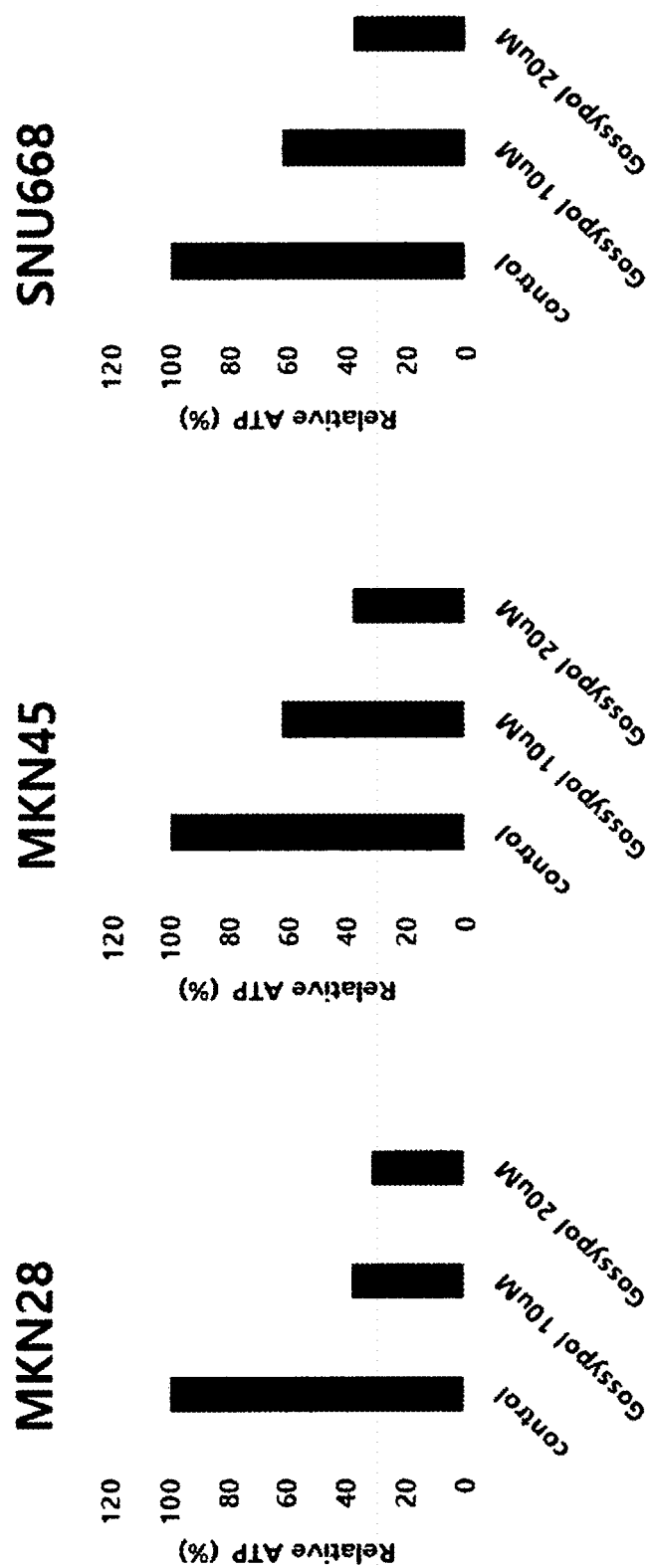
FIG. 2 shows the results of examining the ATP synthesis inhibitory effects of gossypol against stomach cancer cell lines in an example of the present invention.

Each of MKN28, MKN45 and SNU668 cell lines ($1\times10^3$ to $1\times10^4$ cells/plate) was cultured in a 60 mm culture dish for 24 hours, treated with 0, 10 or 20 μM of gossypol, and then additionally cultured for 48 hours. Next, the cells were harvested, counted, diluted in 100 μl of RPMI buffer containing 10 vol % FBS, and then transferred to each well of 96-well plate. To each well containing the cells, 100 μl of assay buffer (rL/L reagent+reconstitution buffer) in the Promega ATP assay kit (G7572, Promega, Durham, N.C., USA) was added, after which the emission of fluorescence was determined by measuring the absorbance at 560 nm. The results are shown in FIG. 2.

The experimental results indicated that ATP synthesis in all the stomach cancer cell lines used in the experiment was inhibited in proportion to the concentration of gossypol. This suggests that gossypol effectively reduces energy levels in cancer cells.

Example 1-3: Examination of the Cell Death Promoting Effects of Gossypol Against Stomach Cancer Cells From Examples 1-1 to 1-2 above, it was expected that gossypol would have the effect of promoting the cell death of cancer cells. Thus, the following experiment was performed.

Figure 3:
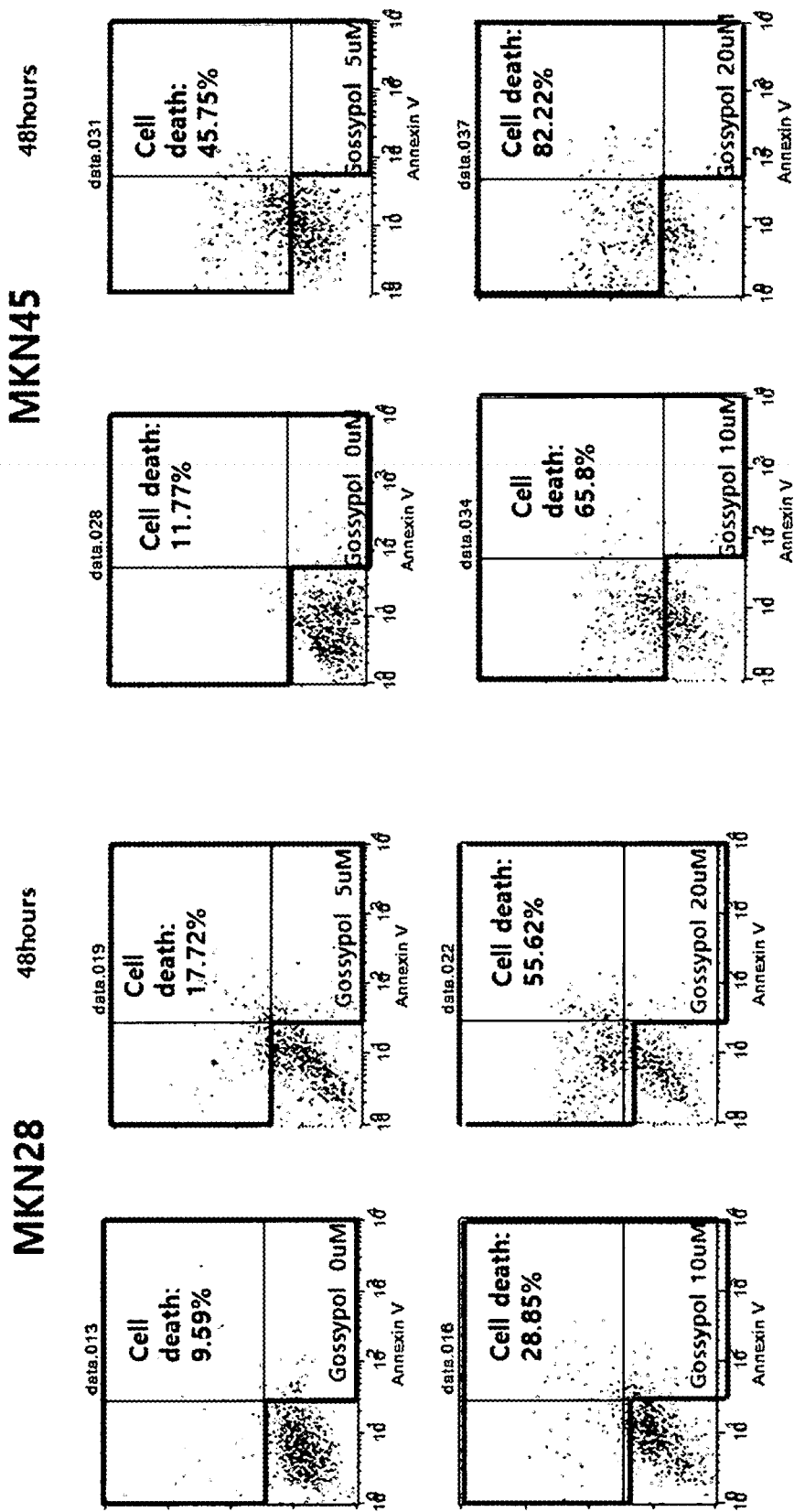
FIG. 3 shows the results of examining the cell death promoting effects of gossypol against stomach cancer cell lines in an example of the present invention.
Figure 4:
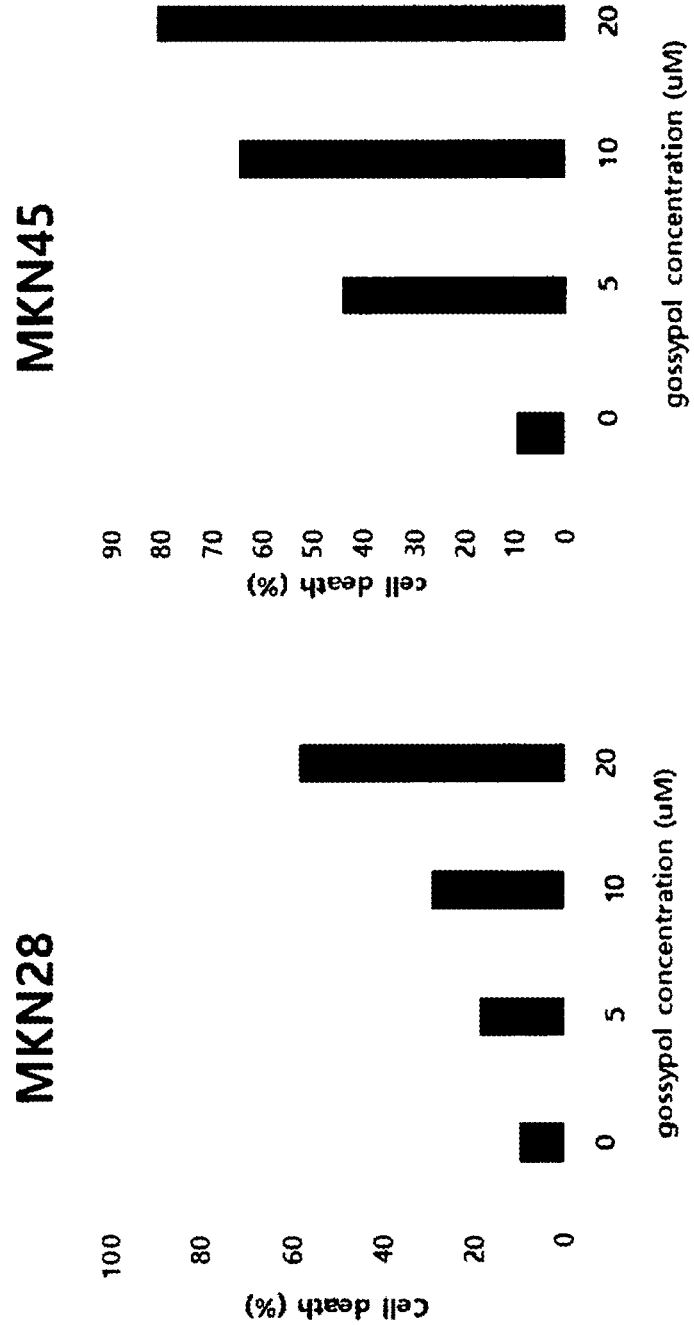
FIG. 4 is a graph showing the results of examining the cell death promoting effects of gossypol against stomach cancer cell lines in an example of the present invention.

Each of MKN28 (moderately differentiated cells) and MKN45 (poorly differentiated cells) cell lines ($1\times10^3$ to $1\times10^4$ cells/plate), described in Example 1-1 above, was cultured in a 100 mm culture dish for 24 hours, and treated with 0, 5, 10 or 20 μM of gossypol, and then diluted in 400 μl of binding buffer (0.1 M Hepes, pH 7.4, 1.4 M NaCl, and 25 mM CaCl$_2$)). The control cells treated with 0 μM of gossypol were divided into four groups which were not stained, stained with Annexin V, stained with PI (propidium iodide) and stained with Annexin V+PI, respectively, and the cells treated with 5, 10 or 20 μM of gossypol were stained with Annexin V+PI. Staining of the cells was performed in a dark room for 10 minutes. The stained cells were subjected to fluorescence activated cell sorting (FACS), thereby determining the ratio of dead cells to total cells. The results are shown in FIGS. 3 and 4 (BD Biosciences, #556547).

The experimental results indicated that MKN28 (moderately differentiated cells) showed cell death percentages of 9.59%, 17.72%, 28.85% and 55.62% at gossypol concentrations of 0, 5, 10 and 20 μM, respectively, and MKN45 (poorly differentiated cells) showed cell death percentages of 11.77%, 45.75%, 65.8% and 82.22%. At all the concentrations of gossypol, the cell death percentage of MKN45 (poorly differentiated cells) was higher than that of MKN28 (moderately differentiated cells), indicating that gossypol has a significant cancer cell inhibitory effect on MKN45 (poorly differentiated cells). In addition, in view of the fact that poorly differentiated cancer includes a large amount of cancer stem cells, it is expected that gossypol will have a significant inhibitory effect on the growth of cancer stem cells.

Figure 5:
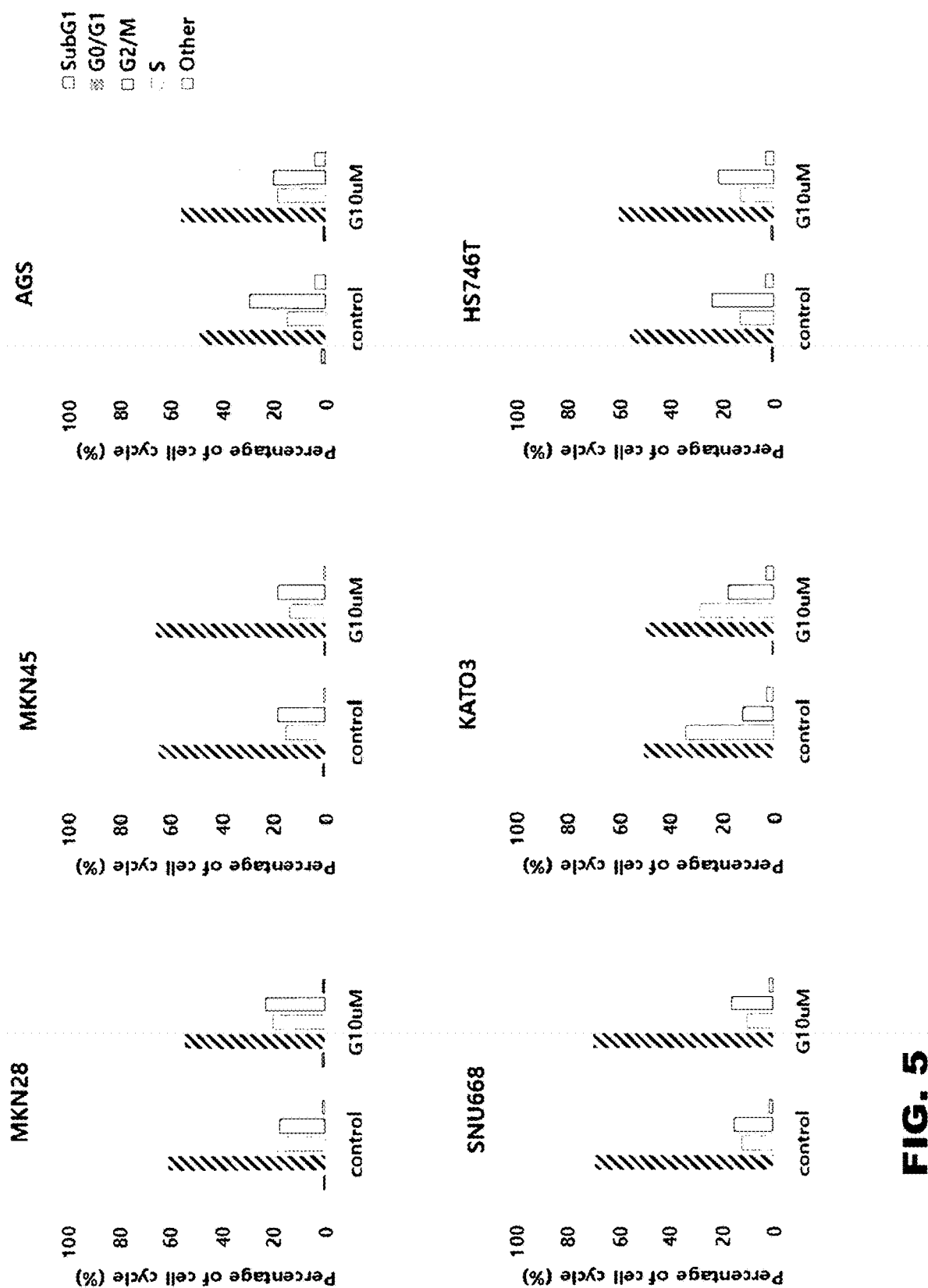
FIG. 5 shows the results of analyzing the cell cycle of gossypol-treated stomach cancer cell lines in an example of the present invention.

Example 1-4: Analysis of Cell Cycle of Stomach Cancer Cells Treated with Gossypol Each of the 6 different stomach cancer cells lines (MKN28, MKN45, AGS, SNU668, Kato3 and HS746T) ($1\times10^3$ to $1\times10^4$ cells/well), described in Example 1-1 above, was cultured in a 100 mm culture dish for 24 hours, and treated with 0 or 10 μM of gossypol, and then further cultured for 24 hours. The cells treated with gossypol were harvested, fixed with 70% ethanol, washed with cold 1×PBS, and then stained with PI+RNase solution (DPBS, pH 7.4) in a dark room for 30 minutes. The cells were subjected to fluorescence activated cell sorting (FACS), and the percentage of each cell cycle was analyzed based on the content of DNA. The results are shown in FIG. 5.

As a result, it could be seen that the sum of sub G1 and G0/G1, which can be interpreted as apoptosis, decreased in the moderately differentiated cells (MKN28) after treatment with gossypol, but increased (MKN45, AGS and HS746T) or was maintained (SNU668 and Kato3) in the poorly differentiated cells compared to before treatment with gossypol.

Example 2: Examination of the Effects of Gossypol Against Stomach Cancer Stem Cells

Example 2-1: Examination of the Proliferation Inhibitory Effects of Gossypol Against Stomach Cancer Stem Cells From Example 1 above, it could be seen that gossypol had a significant inhibitory effect on the growth of poorly differentiated cancer. In addition, in view of the fact that poorly differentiated cancer includes a large amount of cancer stem cells, it is expected that gossypol will also have a significant inhibitory effect on the growth of cancer stem cells. Thus, the following experiment was performed.

Figure 6:
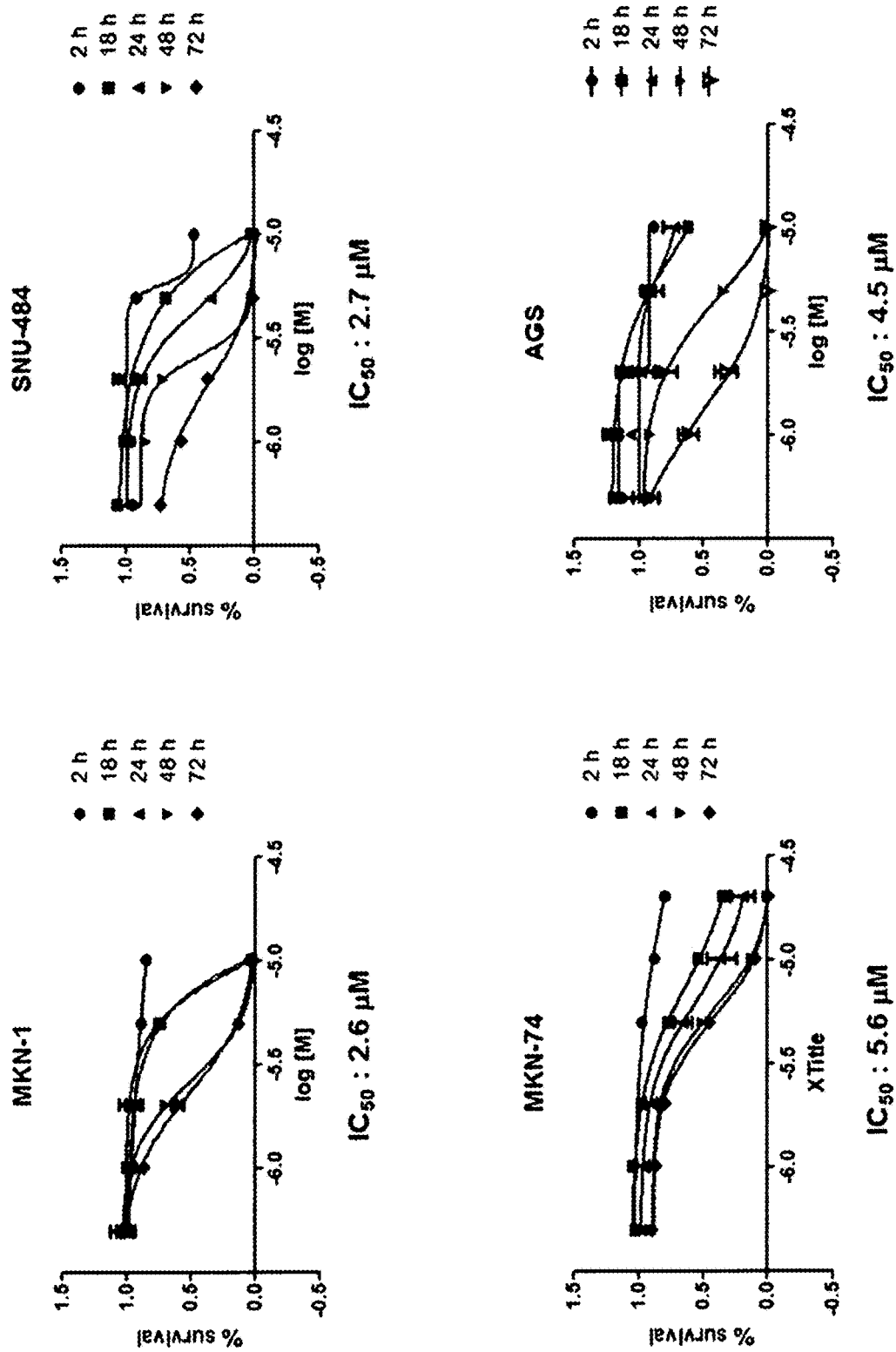
FIG. 6 shows the results of administering gossypol to common stomach cancer cells and stomach cancer stem cells and measuring the $IC_{50}$ concentration of gossypol in an example of the present invention.
Figure 7:
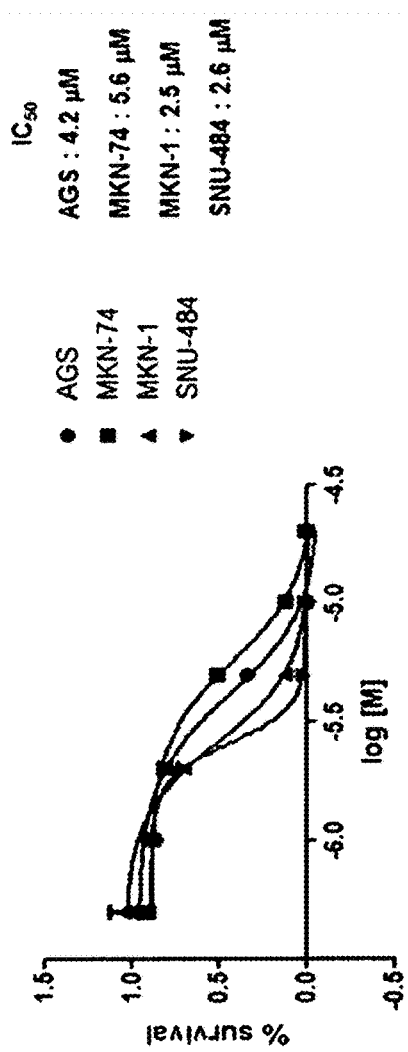
FIG. 7 shows the results of measuring cell survival rate at 48 hours after administering gossypol to common stomach cancer cells and stomach cancer stem cells in an example of the present invention.
Figure 7:
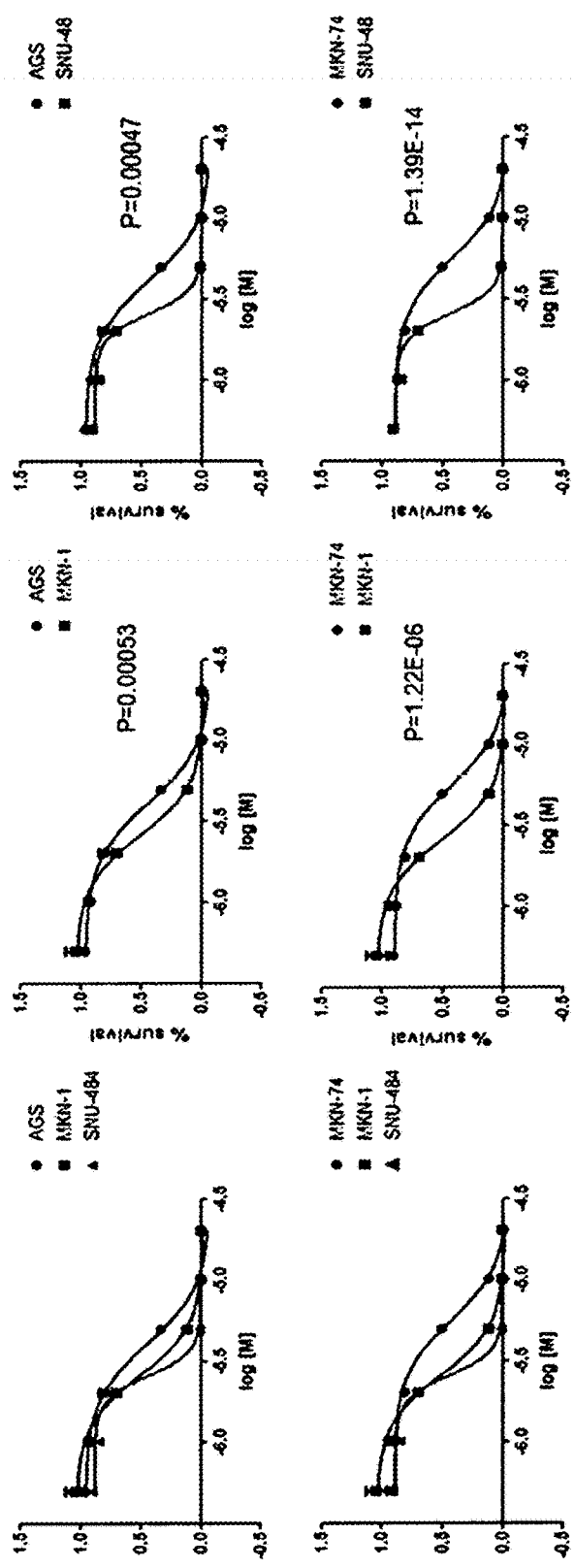

First, in order to examine the growth inhibitory effect of gossypol against stomach cancer stem cells, two types of common stomach cancer cells (AGS and MKN-74) and two types of stomach cancer stem cells (MKN-1 and SNU-484) were prepared. Each type of cells was cultured in a 96-well plate at a density of $1\times10^3$ to $1\times10^4$ cells/well for 24 hours, and treated with 0, 10, 20, 40 or 60 μM of gossypol, and then further cultured for 48 hours. Next, the cells were fixed with 50 wt % TCA (trichloroacetic acid) at 4° C. for 1 hour, washed with distilled water, and then dried at room temperature for a few minutes. Each well containing the fixed cells was stained with 100 μl of 0.4 wt % sulforhodamine B in 1 vol % acetic acid solution for 10 minutes, and washed four times with 1 vol % acetic acid solution. The stained plate was dried at room temperature, and then 100 μl of 10 mM Tris buffer (pH 7.5) was added to each well, and the eluted pigment was measured for its absorbance at a wavelength of 515 nm. Based on the measured absorbance, the IC$_{50}$ concentration of gossypol, at which the survival rate of each type of cells, is measured, and the results are shown in FIGS. 6 and 7.

The experimental results indicated that the $IC_{50}$ concentrations of gossypol for the stomach cancer stem cells (MKN-1 and SNU-484) were 2.6 mM and 2.7 mM, respectively (average: 2.65 mM), and the $IC_{50}$ concentrations of gossypol for the common stomach cancer cells (MKN-74 and AGS) were 5.6 mM and 4.5 mM, respectively (average: 5.05 mM). From these results, it could be seen that the stomach cancer stem cells were more sensitive to gossypol than the common stomach cancer cells and that the effect of gossypol on the inhibition of cancer cell growth was more significant on the stomach cancer stem cells than on the common cancer cells.

Figure 8:
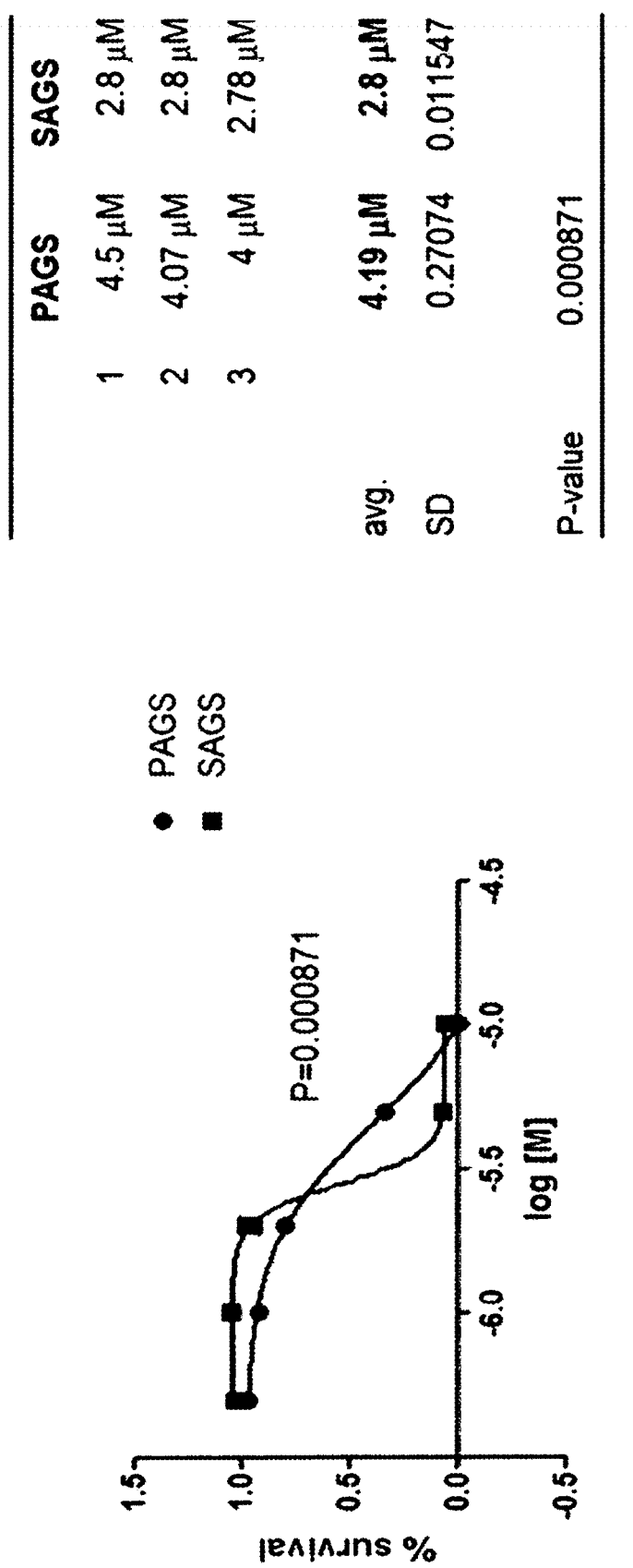
FIG. 8 shows the results of administering gossypol to PAGS and SAGS cells and measuring the $IC_{50}$ concentration of gossypol in an example of the present invention.

Example 2-2: Examination of the Proliferation Inhibitory Effect of Gossypol Against Stem Cells Selected from Cancer Cells On selected AGS cells (hereinafter referred to as SAGS (selected AGS), Cell Death Dis. 2015 Jul. 2; 6:e1805) selected from the common stomach cancer cell line AGS (hereinafter referred to as PAGS (parental AGS)) by analyzing phenotypes, including the cancer stem cell marker expression, tumor spheroid formation and standard anticancer agent resistance of cancer cells that survived under 4 weeks of continuous metabolic stress, and tumor formation in immunosuppressed mice, the growth inhibitory effects of gossypol were examined. Cell culture and survival rate measurement methods were performed in the same manner as Example 2-1. The experimental results indicated that the $IC_{50}$ concentration of gossypol for PAGS was 4.2 mM, whereas the $IC_{50}$ concentration of gossypol for SAGS having the nature of cancer stem cells was 2.8 mM, suggesting that the sensitivity of cells to gossypol significantly differs depending on whether the cells have the nature of stem cells, even though the cells are cells of the same origin. The results are shown in FIG. 8.

Example 3: Examination of the Effect of Co-Administration of Gossypol and Conventional Drug Against Stomach Cancer Cells

Figure 9:
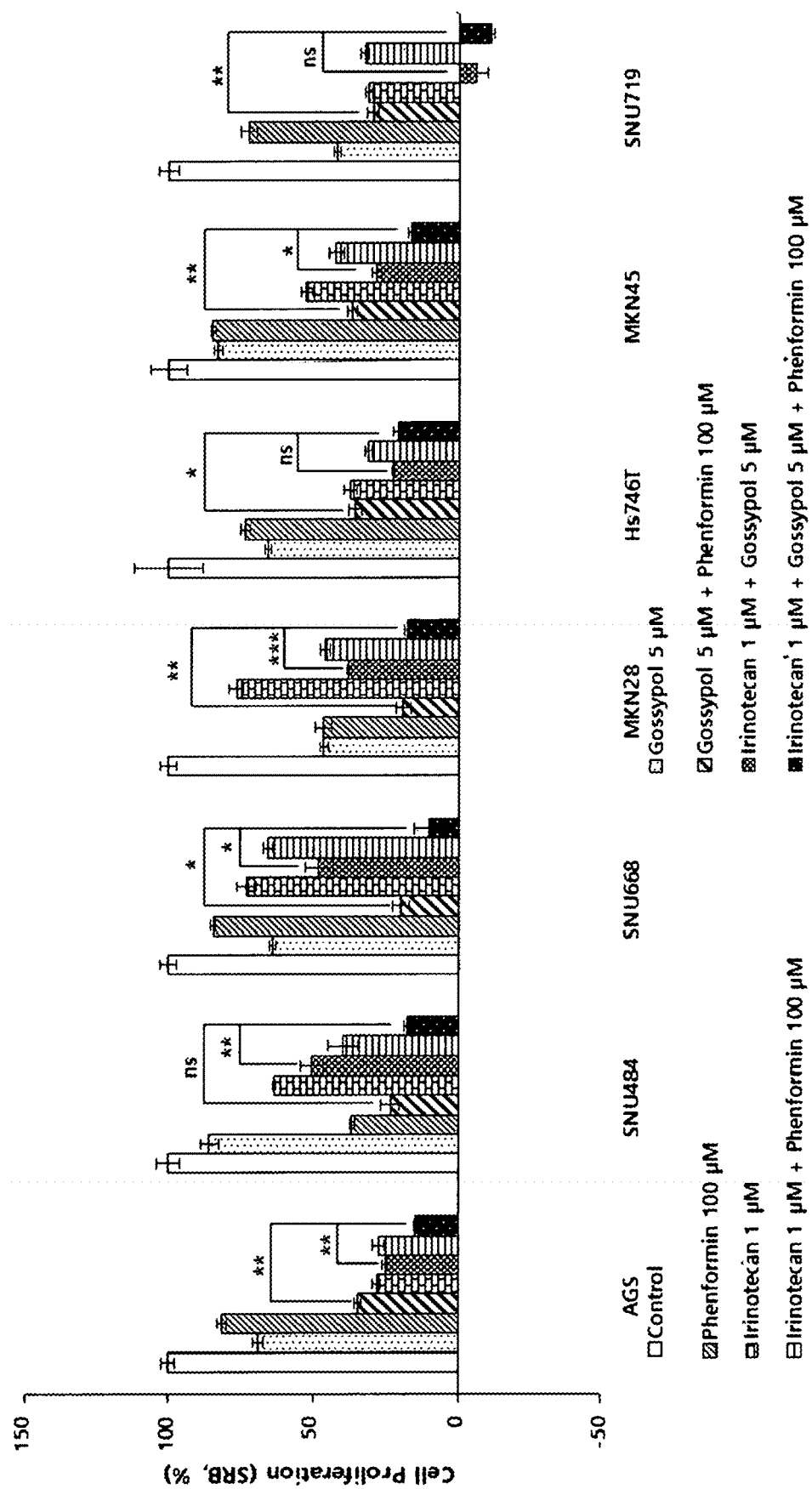
FIG. 9 shows the results of examining the cell growth inhibitory effects of co-administration of gossypol and conventional drugs against stomach cancer cell lines in an example of the present invention.

Example 3-1: Analysis of Growth of Stomach Cancer Cells Co-Treated with Gossypol and Conventional Drug Each of AGS, SNU484, SNU668, MKN28, HS746T, MKN45 and SNU719 stomach cancer stem cells was seeded into a 96-well plate at a density of $5 \times 10^3$ to $4 \times 10^4$ cells/well and cultured for 24 hours. Next, gossypol, phenformin and irinotecan drugs were inoculated into each well as shown in Table 3 below, and the cells were further cultured for 24 hours. Thereafter, the cells were fixed with 50 vol % TCA (trichloroacetic acid; final concentration: 10% TCA) at 4° C. for 1 hour, washed with distilled water, and then dried at room temperature for a few minutes. Each well containing the fixed cells was stained with 100 µl of 0.4 wt % sulforhodamine B in 1 vol % acetic acid solution for 10 minutes, and washed four times with 1 vol % acetic acid solution. The stained plate was dried at room temperature, and then 100 µl of 10 mM Tris buffer (pH 7.5) was added to each well, and the eluted pigment was measured for its absorbance at a wavelength of 515 nm. FIG. 9 shows the inhibitory effects on growth of the stomach cancer cell lines, measured as described above.

TABLE 3

| Experimental Example | Drug administered |
| --- | --- |
| Control | Administered with no drug |
| Experimental Example 1 | Administered with 5 µM of gossypol |
| Experimental Example 2 | Administered with 100 µM of phenformin |
| Experimental Example 3 | Administered with 5 µM of gossypol + 100 µM of phenformin |
| Experimental Example 4 | Administered with 1 µM of irinotecan |
| Experimental Example 5 | Administered with 1 µM of irinotecan + 5 µM of gossypol |
| Experimental Example 6 | Administered with 1 µM of irinotecan + 100 µM of phenformin |
| Experimental Example 7 | Administered with 1 µM of irinotecan + 5 µM of gossypol + 100 µM of phenformin |

The experimental results indicated that when each of gossypol, phenformin and irinotecan was administered alone, it showed various anticancer effects depending on the cell line. When two selected from among the three drugs were used in combination, Experimental Example 3 (gossypol+phenformin) showed the effect of relatively stably inhibiting the growth of the stomach cancer cells, but other combinations showed various effects depending on the cell line. However, it could be seen that when all the three drugs were administered in combination (Experimental Example 7), they showed a cell growth inhibitory effect of at least 80% against all the cell lines used in the experiment.

Figure 10:
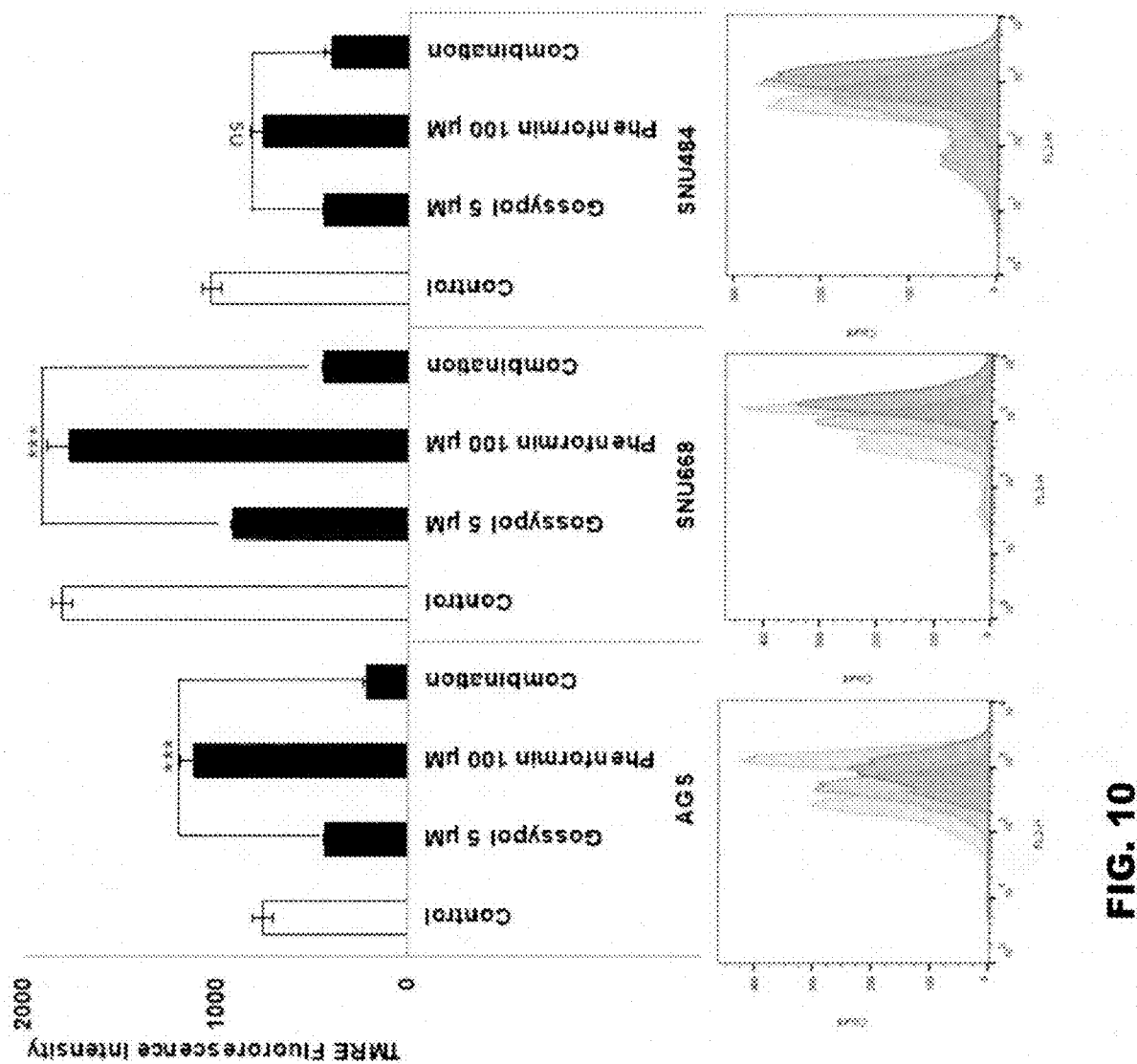
FIG. 10 shows the results of confirming a reduction in intracellular mitochondrial activity after co-administration of gossypol and conventional drugs to stomach cancer cell lines in an example of the present invention.

Example 3-2: Analysis of Mitochondrial Activity of Stomach Cancer Cells Co-Treated with Gossypol and Conventional Drug For the cells of control and Experimental Examples 1 to 7 of Example 3-1 above, the analysis of mitochondrial membrane activity was performed. Mitochondrial membrane activity is used as a marker of intracellular energy production. First, 20 minutes before the treatment of each cell sample with the drug was completed, 100 nM TMRE (tetramethylrodamine ester, ab113852, Abcam) was added to the culture medium. The cells were washed three times with cold PBS, and then the fluorescence intensity of the cells was measured by flow cytometry using a 585 nm (FL-2) channel. The results are shown in FIG. 10.

The experimental results indicated that when gossypol, phenformin and irinotecan were administered in combination, mitochondrial activity was significantly decreased compared to when each of gossypol and phenformin administered alone. This suggests that energy production in the cancer cells was reduced.

Figure 11:
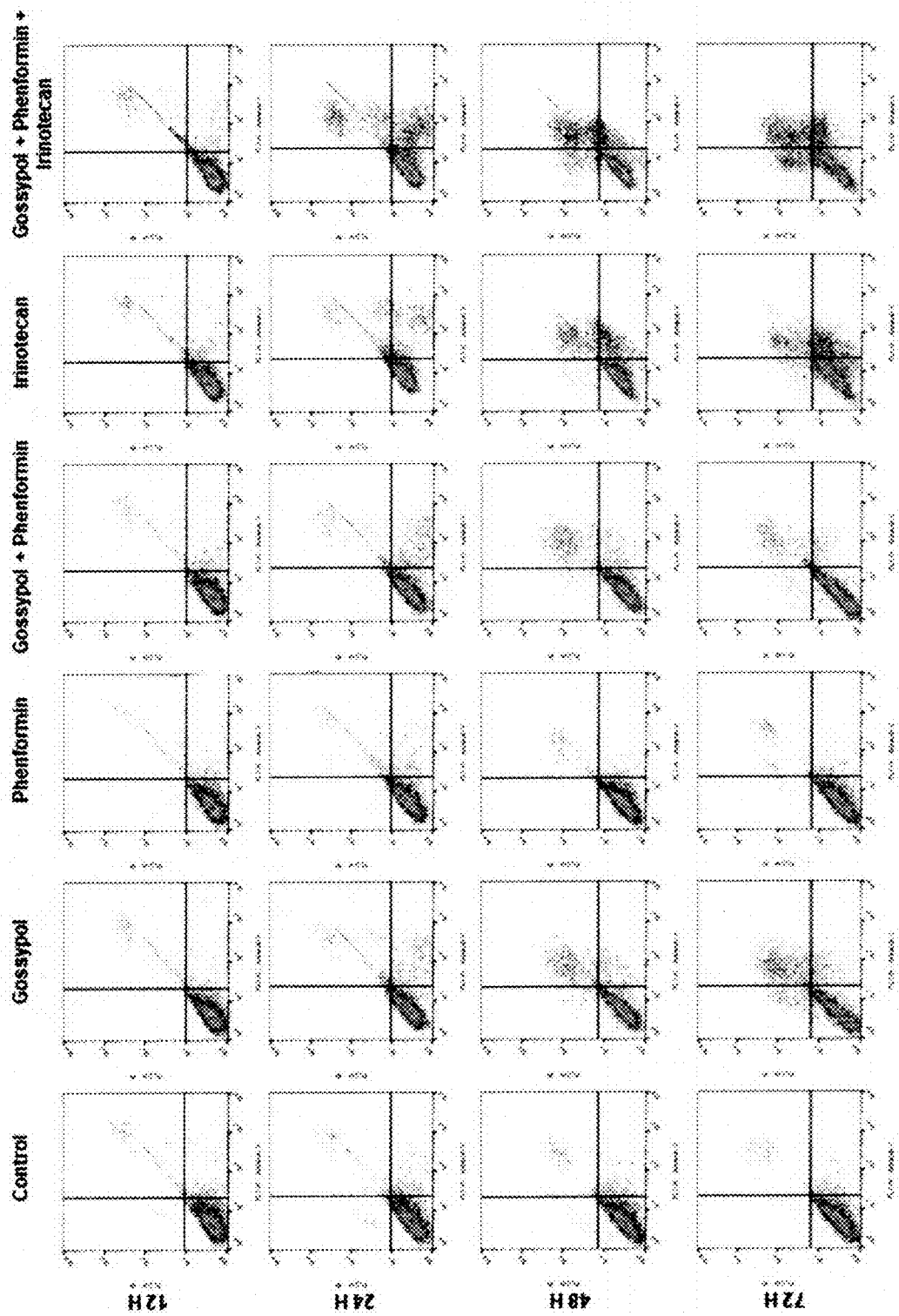
FIG. 11 shows the results of examining the cell death effects of co-administration of gossypol and conventional drugs against stomach cancer cell lines in an example of the present invention.
Figure 12:
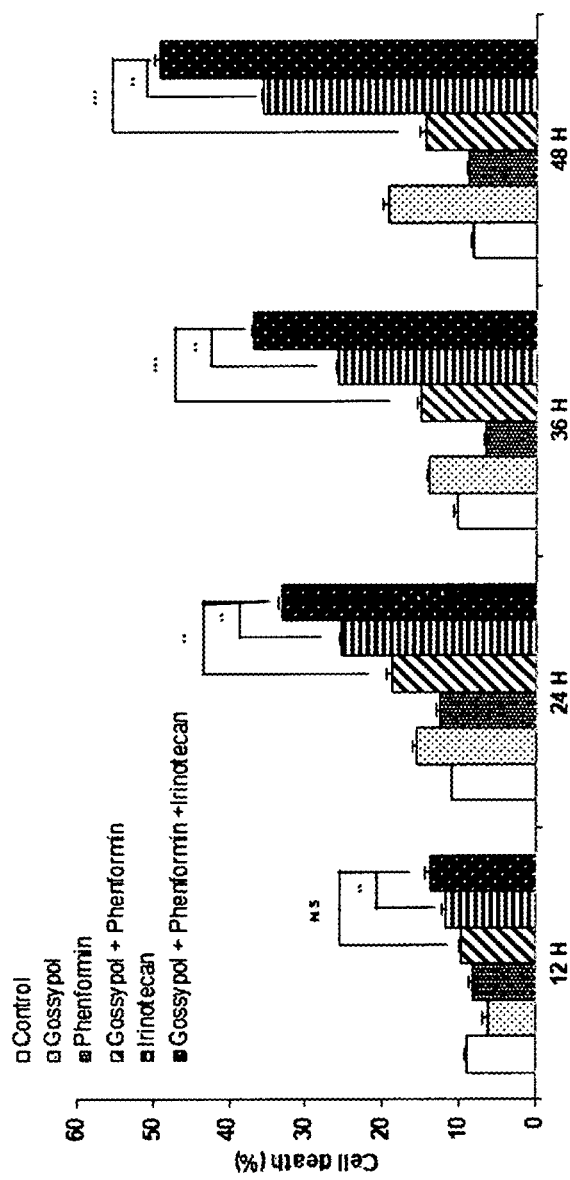
FIG. 12 is a graph showing the results of examining the cell death effects of co-administration of gossypol and conventional drugs against stomach cancer cell lines in an example of the present invention.

Example 3-3: Analysis of Cell Death of Stomach Cancer Cells Co-Treated with Gossypol and Conventional Drug 12, 24, 48 and 72 hours after each drug was administered to the cells of control and Experimental Examples 1 to 7 of Example 3-1 above, a sample was collected and cell death analysis was performed using the sample. First, the cells were washed with cold PBS, centrifuged at 1400 rpm for 3 minutes, and then re-suspended at a concentration of $1 \times 10^6$ cells/ml. 100 µl of the cell suspension was transferred into a 5 ml culture tube, and 5 µl of each of Annexin V-FITC and PI staining dyes was added thereto and incubated in a dark place at room temperature for 15 minutes. Next, 400 µl of 1× binding buffer was added thereto, and the resulting cell suspension was analyzed with a FACS flow cytometer (BD Falcon, Bedford, Mass., USA). The FACS results and a graph expressed in terms of numerical values are shown in FIGS. 11 and 12. The experimental results indicated that when gossypol, phenformin and irinotecan were administered in combination, the death of the cancer cells significantly increased at all the time points compared to when each of gossypol, phenformin and irinotecan was administered alone or when gossypol and phenformin were administered in combination.

From the results of Examples 1 to 3 above, it could be seen that gossypol had a significant effect of inhibiting the proliferation of cancer cells including cancer stem cells and promoting cell death. In addition, it was shown that when phenformin and irinotecan were used in combination with gossypol, the effect on cancer cell death significantly increased.

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereof.

INDUSTRIAL APPLICABILITY

The present invention is directed to a pharmaceutical composition for treatment of cancer and cancer stem cells, which contains a polyphenolic compound as an active ingredient. The pharmaceutical composition according to the present invention is very effective for the treatment and improvement of prognosis of cancer stem cells or cancer tissues including large amounts of cancer stem cells such as poorly differentiated cancer stem cells. In addition, it was found that when the polyphenolic compound, a biguanide-based compound and an anticancer drug were administered to cancer cell in combination, the effect of inhibiting cancer cell growth was significantly increased compared to when they were administered alone, suggesting that the polyphenolic compound will be widely used in the cancer treatment field.

The invention claimed is:

1. A method for preventing or treating stomach cancer, comprising administering to a subject in need of such treatment with an effective amount of a pharmaceutical composition which contains gossypol, phenformin, and irinotecan as active ingredients.

2. The method of claim 1, wherein the cancer includes cancer stem cells.

3. The method of claim 1, wherein the treating includes inhibiting an increase in the number of cancer cells including cancer stem cells, or inhibiting an increase in the amount of the cancer cells, or killing cells, or reducing or maintaining the size of a cancer tissue including cancer stem cells, or inhibiting the development of new blood vessels in a cancer tissue including cancer stem cells.

* * * * *